(12) United States Patent
Jamruszka-Lewis

(10) Patent No.: US 9,456,554 B2
(45) Date of Patent: Oct. 4, 2016

(54) METHOD OF SEPARATING PLANT GERMINANTS FROM GELLED MEDIA

(71) Applicant: Weyerhaeuser NR Company, Federal Way, WA (US)

(72) Inventor: Amy M. Jamruszka-Lewis, Sumner, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 193 days.

(21) Appl. No.: 13/926,172

(22) Filed: Jun. 25, 2013

(65) Prior Publication Data

US 2014/0000160 A1  Jan. 2, 2014

Related U.S. Application Data

(60) Provisional application No. 61/665,133, filed on Jun. 27, 2012.

(51) Int. Cl.
*A01G 1/00* (2006.01)
*A01C 21/00* (2006.01)
*A01H 4/00* (2006.01)

(52) U.S. Cl.
CPC ............ *A01G 1/001* (2013.01); *A01C 21/00* (2013.01); *A01H 4/00* (2013.01); *A01H 4/008* (2013.01)

(58) Field of Classification Search
None
See application file for complete search history.

(56) References Cited

U.S. PATENT DOCUMENTS

| | | |
|---|---|---|
| 4,408,549 A | 10/1983 | Qvarnstrom |
| 4,957,866 A | 9/1990 | Gupta |
| 5,034,326 A | 7/1991 | Pullman |
| 5,036,007 A | 7/1991 | Gupta |
| 5,041,382 A | 8/1991 | Gupta |
| 5,215,550 A | 6/1993 | Tesch |
| 5,236,841 A | 8/1993 | Gupta |
| 5,294,549 A | 3/1994 | Pullman |
| 5,482,857 A | 1/1996 | Gupta |
| 5,563,061 A | 10/1996 | Gupta |
| 5,564,224 A | 10/1996 | Carlson |
| 5,687,504 A | 11/1997 | Carlson |
| 5,701,699 A | 12/1997 | Carlson |
| 5,821,126 A | 10/1998 | Durzan |
| 6,119,395 A | 9/2000 | Hartle |
| 7,530,197 B2 * | 5/2009 | Timmis ............... A01H 1/04 47/57.6 |
| 7,610,155 B2 | 10/2009 | Timmis |
| 7,665,243 B2 * | 2/2010 | Nehra et al. ............. 47/1.01 R |
| 2004/0035161 A1 * | 2/2004 | Wagenaar ..................... 71/28 |
| 2006/0260015 A1 | 11/2006 | Becwar et al. |
| 2007/0269096 A1 | 11/2007 | Timmis |
| 2009/0280566 A1 | 11/2009 | Carpenter et al. |
| 2010/0024081 A1 | 1/2010 | Clark et al. |
| 2011/0078819 A1 | 3/2011 | Bullock |
| 2012/0258536 A1 | 10/2012 | Aidun |
| 2013/0168296 A1 * | 7/2013 | Swanda et al. .................. 209/2 |

OTHER PUBLICATIONS

Roberts et al. 11. A deliver system for naked somatic embryos of interior spruce. Automation and Environmental Control in Plant Tissue Culture (1995) 245-256.*
Fira et al. Ex-vitro acclimation of some horticultural species in hydroculture. Bulletin UASVM Horticulture, 66(1) 2009.*

* cited by examiner

*Primary Examiner* — June Hwu
(74) *Attorney, Agent, or Firm* — Perkins Coie LLP

(57) ABSTRACT

The present disclosure provides methods of separating plant germinants from gelled germination medium.

18 Claims, No Drawings

METHOD OF SEPARATING PLANT GERMINANTS FROM GELLED MEDIA

CROSS-REFERENCE TO RELATED APPLICATION

This application is entitled to and claims the benefit of priority under 35 U.S.C. §119 from U.S. Provisional Patent Application Ser. No. 61/665,133 filed Jun. 27, 2012, and titled "Methods of Separating Plant Germinants from Gelled Media," the contents of which are incorporated herein by reference.

BACKGROUND

Modern silviculture often requires the planting of large numbers of genetically identical plants that have been selected to have advantageous properties. Production of new plants by sexual reproduction, which yields botanic seeds, is usually not feasible. Asexual propagation, via the culturing of somatic or zygotic embryos, has been shown for some species to yield large numbers of genetically identical embryos, each having the capacity to develop into a normal plant.

Somatic cloning is the process of creating genetically identical plants from plant tissue other than male and female gametes. In one approach to somatic cloning, plant tissue is cultured in an initiation medium that includes hormones, such as auxins and/or cytokinins, to initiate formation of embryogenic tissue, such as an embryogenic suspensor mass, that is capable of developing into somatic embryos. An embryogenic suspensor mass, or ESM, has the appearance of a whitish translucent mucilaginous mass and contains a plurality of early stage embryogenic tissue. The embryogenic tissue is further cultured in a multiplication medium that promotes multiplication and mass production of the embryogenic tissue. The embryogenic tissue is then cultured in a development medium that promotes development and maturation of cotyledonary somatic embryos that can, for example, subsequently be placed on germination medium to produce germinants, which in turn can be transferred to soil for further growth. Alternatively, the cotyledonary somatic embryos can be placed within manufactured seeds and sown in soil where they germinate to yield seedlings. Manufactured seeds are described, for example, in U.S. Pat. Nos. 5,564,224; 5,687,504; 5,701,699; and 6,119,395.

The somatic embryogenesis process is laborious and inefficient. For example, one of the more labor intensive steps in the embryogenesis process is the harvesting of individual plant germinants from gelled germination medium by a skilled technician. The harvesting process is a tedious job that is time consuming and causes ergonomic stress to workers. Further, it poses a major production bottleneck when the ultimate desired output can be in the thousands of plants.

There is a continuing need to improve the efficiency of harvesting plant germinants in order to reduce labor and technician fatigue, reduce the risk of worker injury, and increase the production rate to achieve commercial scale.

The present disclosure describes methods of separating plant germinants en masse from gelled germination medium.

SUMMARY

Methods of separating plant germinants from gelled germination medium are provided. Each of the methods includes the steps of: (a) placing a gelled germination medium having a plurality of plant germinants embedded in the gelled germination medium, onto a mesh material such that the plurality of plant germinants are proximate to the mesh material; (b) applying a first wash solution to the gelled germination medium with a force sufficient to break-up and dislodge the gelled germination medium from the plurality of plant germinants; and (c) continuing to apply the first wash solution such that the gelled germination medium is separated from the plurality of plant germinants, and the plurality of plant germinants remain on mesh material.

The steps of the methods can be performed manually or can be automated.

The methods of the present disclosure further include the step of placing the mesh material having a plurality of plant germinants disposed on the mesh material proximate to a container and applying a second wash solution to the plurality of plant germinants to dislodge the plurality of plant germinants from the mesh material and to wash the plurality of plant germinants into the container to collect the germinants.

The methods also include subsequently transferring the plurality of plant germinants to soil to produce plants. The plurality of plant germinants can also be stored in a holding solution under suitable environmental conditions for a period of time before transferring the plurality of plant germinants to soil.

DETAILED DESCRIPTION

As used herein, the term "germinant" refers to an immature plant that possesses a well developed radicle and a growing epicotyl, both readily apparent to the naked eye, and is ready for transferring to soil. For example, plant germinants typically have a radicle greater than 3 mm in length and an epicotyl of about 10 mm in length or greater.

As used herein, the term "epicotyl" refers to the shoot portion of a germinant located above the cotyledons.

As used herein, the term "radicle" refers to the part of a germinant that develops into the primary root of the resulting plant.

As used herein, the term "mesh material" refers to any perforated material having openings to allow for the flow of a liquid through the material.

A somatic embryogenesis process is a process to develop plant embryos in vitro. Methods for producing plant somatic embryos are known in the art and have been previously described (see, e.g., U.S. Pat. Nos. 4,957,866; 5,034,326; 5,036,007; 5,041,382; 5,236,841; 5,294,549; 5,482,857; 5,563,061; and 5,821,126). Generally, the somatic embryogenesis process includes the steps of (1) initiation or induction, to initiate formation of embryogenic tissue, such as an embryogenic suspensor mass (ESM), which is a white mucilaginous mass that includes early stage embryos having a long, thin-walled suspensor associated with a small head with dense cytoplasm and large nuclei; (2) multiplication, sometimes referred to as maintenance, to multiply and mass produce embryogenic tissue; (3) development, to develop and form mature cotyledonary somatic embryos; and (4) post development steps such as separation, singulation, stratification, germination, placement into manufactured seeds, and transferring to soil for further growth and development.

The typical somatic embryogenesis process is labor intensive. Efforts have been made to automate and scale-up the process to facilitate the production of somatic plant embryos in large scale, perhaps tens of thousands at a time. For example, the multiplication step can be carried out in a commercial-scale liquid bioreactor. At the end of the multiplication step, embryogenic tissue in the form of an embryogenic suspensor mass can be transferred to development medium for a period of time to develop into a plurality of cotyledonary embryos. At the end of the development period, cotyledonary embryos can be transferred from development medium to germination medium. Automated methods for the harvesting of plant cotyledonary embryos from development medium are described for example in U.S. Pat. No. 7,530,197.

After the development period, mature cotyledonary embryos can be transferred to germination medium to develop into immature plants or plant germinants. One of the more labor intensive steps in the embryogenesis process is the harvesting of individual plant germinants from gelled germination medium. Typically, a skilled technician evaluates the morphological features of each germinant, such as size, radicle and epicotyl development, color, and the like, and manually plucks desirable germinants from the germination medium with a pair of forceps or other tool, a single germinant at a time. This is a highly skilled yet tedious job that is time consuming and expensive. The plucking process is also ergonomically stressful because some amount of pulling force must be applied to the plant germinants, which have well-developed radicles embedded in the germination medium.

In one aspect, the present disclosure provides methods for separating plant germinants from gelled germination medium. Each of the methods includes the steps of: (a) placing a gelled germination medium having a plurality of plant germinants embedded in the gelled germination medium onto a mesh material such that the plurality of plant germinants are proximate to the mesh material; (b) applying a first wash solution to the gelled germination medium with a force sufficient to break-up and dislodge the gelled germination medium from the plurality of plant germinants; and (c) continuing to apply the first wash solution such that the gelled germination medium is separated from the plurality of plant germinants, and the plurality of plant germinants remain on the mesh material.

In one embodiment, the gelled germination medium is inverted onto the mesh material such that the plurality of plant germinants are opposite to and facing the mesh material. In one embodiment, the first wash solution is applied to the bottom surface of the gelled germination medium.

The steps of the methods can be performed manually or can be automated.

The gelled germination medium can be separated from the plurality of plant germinants using a first wash solution, such as water or an isotonic nutrient solution. The first wash solution can be applied in a variety of ways. The first wash solution can be applied, for example, as a coarse spray, a fine spray, a stream, or a combination thereof. The volume (flow-rate) and pressure of the first wash solution can be varied as needed. The first wash solution can be applied in the form of a forceful spray to break-up the gelled germination medium. The first wash solution can be applied so as to cover a wide area, or can be applied so as to be directed to and concentrated on a small area. As the gelled germination medium is separated from the plant germinants, the volume and pressure of the first wash solution can be reduced so as not to damage the germinants.

During the separation process, the first wash solution can continue to be applied to the plurality of plant germinants to facilitate removal and washing away of any undesirable material, such as residual gelled germination medium, through the openings of the mesh material. In some embodiments, more than one mesh material may be used to separate the germinants from the gelled germination medium and to sort the germinants according to size.

Sorting according to size can be accomplished by using mesh materials with various opening sizes. The opening sizes of the mesh material can be selected so as to capture the desired size plant germinants, while allowing gelled germination medium, undersized plant germinants, and other debris to flow through the openings of the mesh material.

In some embodiments, the mesh material can be arranged in a stack such that a first mesh material with a first mesh opening size is placed on top of a second mesh material with a second mesh opening size that is smaller than the first mesh opening size. By way of example, the first mesh material can be of a mesh opening size such that germinants of the desired size, undersized germinants, and the gelled germination medium pass through the first mesh material, and germinants that are larger than the desired size are captured on the surface of the first mesh material. The second mesh material can be of a mesh opening size such that germinants of the desired size are captured on the second mesh material, and undersized germinants and the gelled germination medium pass the second mesh material. Typically, a mesh material having an opening size from about 3 mm to about 25 mm can be used. For example, mesh opening sizes of 10 mm can be used.

The mesh material can be, for example, a screen or sieve. The mesh material can be made of any material that is non-toxic to the plant germinants and that can withstand exposure to liquid and the force of the wash solution applied to separate the plant germinants from the gelled germination media. Examples of useful mesh materials include for example, nylon, stainless steel or plastic.

In some embodiments, the gelled germination media with disposed plant germinants is contained in a container. A sharp tool can be used to loosen and dislodge the gelled germination media from the container and to facilitate transferring the gelled germination media to the mesh material.

In some embodiments, the methods of the present disclosure further include the step of placing the mesh material having a plurality of plant germinants disposed on surface of the mesh material proximate to a container and applying a second wash solution to the plurality of plant germinants to dislodge the plurality of plant germinants from the mesh material and wash the plurality of plant germinants into the container to collect the germinants. The second wash solution can be applied with sufficient volume and pressure so as to remove the plurality of plant germinants from the mesh material but not damage the germinants. The second wash solution can be any suitable liquid, e.g., water, nanopure water, isotonic nutrient solution, or liquid germination medium. The nutrient solution can include hormones and vitamins to encourage rooting and growth, for example auxins or micronutrients. The nutrient solution can also include antibiotics and anti-fungal agents to prevent contamination. The first and second wash solutions can be the same or different.

In some embodiments, the methods of the present disclosure further include the step of removing the plurality of plant germinants from the container and transferring the plurality of plant germinants to one or more containers of a holding solution. The holding solution can be any suitable liquid, e.g., water, nanopure water, isotonic nutrient solution, or liquid germination medium. The nutrient solution can include hormones and vitamins to encourage rooting and growth, for example auxins or micronutrients. The nutrient solution can also include antibiotics and anti-fungal agents to prevent contamination. The plurality of plant germinants can be accumulated and stored in the holding solution for a period of time until it is convenient to transfer them to a potting medium as transplants for further growth. For example, the plurality of plant germinants can be transferred to soil in a greenhouse for further growth before being transplanted to an outdoor site. In some embodiments, the methods of the present disclosure further include the step of transferring the plurality of plant germinants to soil to produce plants.

Plant germinants suitable for use in the methods of the invention can be from any plant species, such as dicotyledonous or monocotyledonous plants, gymnosperms, and the like. Conifer germinants are suitable for use in the methods of the invention and can be from any conifer species including, but not limited to, species within the family Pinaceae, and genera *Pinus, Picea, Tsuga, Pseudotsuga, Thuja, Juniperis, Larix,* and *Sequoia*.

In some embodiments, the plurality of plant germinants are conifer plant germinants. In some embodiments, the plurality of conifer plant germinants are plant germinants of the family Pinaceae. In some embodiments, the plurality of conifer plant germinants are Loblolly-pine plant germinants. In some embodiments, the plurality of conifer plant germinants can be Douglas-fir plant germinants. The methods of the present disclosure provide a simple process to separate plant germinants from gelled germination medium. The methods of the present disclosure eliminate the need to utilize skilled technicians to select plant germinants that are likely to produce plants, and therefore remove subjectivity from the process. Furthermore, the methods of the present disclosure can produce a large number of plant germinants suitable for developing into plants, while significantly increasing productivity, reducing labor costs, and reducing risk of injury to workers, when compared to the methods generally used in the art of selecting plant germinants according to certain criteria and hand-plucking the plant germinants from germination medium. For example, generally, it takes a skilled technician about one hour to select and hand-pluck about 800 plant germinants from gelled germination medium.

In contrast, using the methods of the present disclosure, the same number of plant germinants can be separated from germination medium in about ten minutes, which is about a 5-fold increase in productivity.

Typically many thousands of plant germinants are transferred to soil at the same time for clonal field tests. The methods of the present disclosure thus enable the production of plant germinants suitable for transferring to soil at commercial scale, while significantly reducing costs, and increasing productivity and worker well-being.

EXAMPLES

Example 1

This example illustrates the results obtained when a plurality of Loblolly pine plant germinants were separated en masse from gelled germination medium using an embodiment of the present disclosure.

Loblolly pine plant germinants of five different genotypes were produced according to standard methods known in the art. The Loblolly pine plant germinants were separated from gelled germination medium according to one of the following methods:

Method 1

Control

Plant germinants were individually hand-plucked from gelled germination medium using a tool, and were subsequently potted and transferred to a greenhouse.

Method 2

Gelled germination medium was separated from plant germinants using the methods of the present disclosure. In this Method 2, the gelled germination medium was separated from a plurality of pine plant germinants using water as a first wash solution. The water was applied as a coarse spray using a hand-held nozzle, and the mesh material had a opening size of about 10 mm. The plant germinants were then sprayed with water to remove the germinants from the mesh material to collect the germinants and water into a container. The plant germinants were retrieved from the water, and were subsequently potted and transferred to a greenhouse.

Method 3

Gelled germination medium was separated from plant germinants using the methods of the present disclosure. In this Method 3, the gelled germination medium was separated from a plurality of pine plant germinants using water as a first wash solution. The water was applied as a coarse spray using a hand-held nozzle, and the mesh material had a opening size of about 10 mm. The plant germinants were then hand-plucked from the mesh material using forceps, and were subsequently potted and transferred to a greenhouse.

Table 1 illustrates the percent survival of plant germinants, separated from gelled germination medium according to Methods 1-3 above, assessed 6 weeks after transferring to soil.

TABLE 1

| Genotype | Method 1 | Method 2 | Method 3 |
| --- | --- | --- | --- |
| A | 100 | 100 | 96.2 |
| B | 94.9 | 100 | 97.5 |
| B | 98.9 | 93.3 | 92.6 |
| C | 20 | 33.3 | NA |
| D | 95.6 | 100 | 93.4 |
| E | 93.2 | 70.7 | 89.2 |
| Average percent survival including genotype C | 83.8 | 82.9 | NA |
| Average percent survival excluding genotype C | 97.1 | 94 | 94.2 |

The results in Table 1 indicate that there is no statistically significant difference in survival of plant germinants separated from gelled germination medium using the methods of the present disclosure to separate plant germinants from gelled germination medium and to dislodge the plant germinants from the mesh material when compared to the conventional hand-plucking method (Method 1 v. Method 2, p value=0.87). No statistically significant difference in survival of plant germinants separated from gelled germination medium using the methods of the present disclosure to separate plant germinants from gelled germination medium and hand-plucking the plant germinants from the mesh material was found when compared to the conventional hand-plucking method (Method 1 v. Method 3, p value=0.14).

These results indicate that the methods of the present disclosure do not have a deleterious effect on the survival of plant germinants.

While the preferred embodiment of the invention has been illustrated and described, it will be appreciated that various changes can be made therein without departing from the spirit and scope of the invention.

The invention claimed is:

1. A method of separating a plurality of conifer plant germinants from a gelled germination medium comprising the steps of:
   (a) inverting a gelled germination medium having a plurality of conifer plant germinants embedded in the gelled germination medium onto a mesh material such that the plurality of conifer plant germinants are opposite to and facing the mesh material;
   (b) applying a first wash solution to bottom surface of the gelled germination medium with a force sufficient to break-up and dislodge the gelled germination medium from the plurality of conifer plant germinants; and
   (c) continuing to apply the first wash solution such that the gelled germination medium is separated from the plurality of conifer plant germinants, and the plurality of conifer plant germinants remain on the mesh material.

2. The method of claim 1, wherein the first wash solution is water or an isotonic nutrient solution.

3. The method of claim 1, wherein the first wash solution is applied as a coarse spray, a fine spray, a stream, or a combination thereof.

4. The method of claim 1, wherein the mesh material is located on top of a stack of a plurality of mesh materials, each having a mesh opening size, and wherein the plurality of mesh materials are arranged in the stack according to mesh opening size, in decreasing order, such that the mesh material having the largest mesh opening size is on top of the stack, and the mesh material having the smallest mesh opening size is on the bottom of the stack.

5. The method of claim 4, wherein each mesh material has opening sizes ranging from about 3 mm to about 25 mm.

6. The method of claim 4, wherein the plurality of conifer plant germinants are sorted according to size.

7. The method of claim 1, further comprising placing the mesh material having the plurality of conifer plant germinants disposed on the mesh material proximate to a container and applying a second wash solution to the plurality of conifer plant germinants to dislodge the plurality of conifer plant germinants from the mesh material and wash the plurality of conifer plant germinants into the container.

8. The method of claim 7, wherein the second wash solution is water, nanopure water, isotonic nutrient solution, or liquid germination medium.

9. The method of claim 8, wherein the second wash solution comprises hormones, vitamins, micronutrients, or a combination thereof.

10. The method of claim 9, wherein the second wash solution further comprises antibiotics and/or anti-fungal agents.

11. The method of claim 7, further comprising removing the plurality of conifer plant germinants from the container and transferring the plurality of conifer pant germinants to one or more containers of a holding solution.

12. The method of claim 11, wherein the holding solution is water, nanopure water, isotonic nutrient solution, or liquid germination medium.

13. The method of claim 12, wherein the holding solution comprises hormones, vitamins, micronutrients, or a combination thereof.

14. The method of claim 13, wherein the holding solution further comprises antibiotics and/or anti-fungal agents.

15. The method of claim 11, further comprising storing the plurality of conifer plant germinants in the holding solution.

16. The method of claim 1, further comprising transferring the plurality of conifer plant germinants to soil to produce plants.

17. The method of claim 1, wherein the plurality of conifer plant germinants are plant germinants of the family Pinaceae.

18. The method of claim 17, wherein the plurality of conifer plant germinants are Loblolly-pine plant germinants.

* * * * *